(12) United States Patent
Honda et al.

(10) Patent No.: US 7,771,050 B2
(45) Date of Patent: Aug. 10, 2010

(54) OPHTHALMIC APPARATUS

(75) Inventors: Naoto Honda, Okazaki (JP); Shigekazu Takada, Gamagori (JP); Kazuhiro Yoshimura, Toyohashi (JP); Naoki Isogai, Nishio (JP); Akihiro Hayashi, Toyokawa (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 12/225,736

(22) PCT Filed: Apr. 2, 2007

(86) PCT No.: PCT/JP2007/057397
§ 371 (c)(1),
(2), (4) Date: Sep. 29, 2008

(87) PCT Pub. No.: WO2007/114426
PCT Pub. Date: Oct. 11, 2007

(65) Prior Publication Data
US 2009/0128778 A1  May 21, 2009

(30) Foreign Application Priority Data

| Mar. 31, 2006 | (JP) | ................ 2006-096929 |
| Mar. 31, 2006 | (JP) | ................ 2006-096930 |
| Apr. 12, 2006 | (JP) | ................ 2006-110163 |
| Feb. 28, 2007 | (JP) | ................ 2007-050156 |
| Feb. 28, 2007 | (JP) | ................ 2007-050157 |

(51) Int. Cl.
*A61B 3/14* (2006.01)
*A61B 3/10* (2006.01)
*A61B 3/00* (2006.01)

(52) U.S. Cl. ............... 351/208; 351/205; 351/212; 351/245

(58) Field of Classification Search ............ 351/200, 351/205, 208, 211, 212, 221, 245; 600/403–405
See application file for complete search history.

(56) References Cited

U.S. PATENT DOCUMENTS 5,325,135 A * 6/1994 Nakamura et al. .......... 351/212
5,341,575 A * 8/1994 Chisum ...................... 33/608

(Continued)

FOREIGN PATENT DOCUMENTS

CN  2071054 U  2/1991

(Continued)

*Primary Examiner*—Jack Dinh
(74) *Attorney, Agent, or Firm*—Oliff & Berridge, PLC

(57) ABSTRACT

To provide an ophthalmic apparatus capable of performing efficient measurement of a plurality of eye characteristics of an examinee's eye, which comprises a first measurement unit comprising a first measurement system for performing measurement of a first characteristic of the eye, a second measurement unit comprising a second measurement system for performing measurement of a second characteristic of the eye, a measurement unit in which the measurement units are placed such that heights of first and second measurement axes of the respective systems are different from each other, a movement mechanism unit moving the measurement unit in a vertical direction, and a control unit controlling the mechanism unit such that the height of the first measurement axis at the time of first measurement by the first measurement unit becomes almost the same as that of the second measurement axis at the time of second measurement by the second measurement unit.

9 Claims, 6 Drawing Sheets

U.S. PATENT DOCUMENTS

| | | |
|---|---|---|
| 5,463,430 A | 10/1995 | Isogai et al. |
| 5,764,341 A | 6/1998 | Fujieda et al. |
| 6,022,108 A | 2/2000 | Yoshida et al. |
| 6,537,215 B2 | 3/2003 | Miwa |
| 6,755,528 B2 | 6/2004 | Isogai |
| 7,364,298 B2 | 4/2008 | Hayashi et al. |
| 7,399,081 B2 | 7/2008 | Mimura et al. |
| 2005/0157261 A1 | 7/2005 | Hanebuchi et al. |

FOREIGN PATENT DOCUMENTS

| | | |
|---|---|---|
| JP | A-1-265937 | 10/1989 |
| JP | A-6-46999 | 2/1994 |
| JP | A-9-149885 | 6/1997 |
| JP | A-10-71122 | 3/1998 |
| JP | A-2001-61783 | 3/2001 |
| JP | A-2002-34927 | 2/2002 |
| JP | A-2003-169778 | 6/2003 |
| JP | A-2004-313758 | 11/2004 |
| JP | A-2005-185523 | 7/2005 |
| JP | A-2007-144128 | 6/2007 |

* cited by examiner

OPHTHALMIC APPARATUS

TECHNICAL FIELD

The present invention relates to an ophthalmic apparatus which performs measurement of a plurality of eye characteristics.

BACKGROUND ART

Conventionally, a multifunction ophthalmic apparatus which comprises a first measurement unit comprising a first measurement system for performing measurement of a first characteristic of each of examinee's eyes and a second measurement unit comprising a second measurement system for performing measurement of a second characteristic of each of the examinee's eyes is known. In this kind of apparatus, alignment of a measurement axis of the first measurement system is performed with each of the examinee's right and left eyes and the measurement of the first characteristic of each of the examinee's eyes is firstly performed. Then, alignment of a measurement axis of the second measurement system is performed with each of the examinee's right and left eyes and the measurement of the second characteristic of each of the examinee's eyes is secondly performed. Accordingly, the alignment is performed more than once.

DISCLOSURE OF THE INVENTION

Problem to be Solved by the Invention

The present invention has been made in view of the above circumstances and has an object to provide an ophthalmic apparatus capable of performing efficient measurement of a plurality of eye characteristics.

Means for Solving the Problems

To achieve the objects and in accordance with the purpose of the present invention, an ophthalmic apparatus according to a preferred embodiment of the present invention which is arranged to perform measurement of a plurality of eye characteristics of an examinee's eye comprises a first measurement unit comprising a first measurement system for performing measurement of a first characteristic of the examinee's eye, a second measurement unit comprising a second measurement system for performing measurement of a second characteristic of the examinee's eye, a measurement unit in which the first measurement unit and the second measurement unit are placed such that a height of a first measurement axis of the first measurement system and a height of a second measurement axis of the second measurement system are different from each other, a movement mechanism unit arranged to move the measurement unit in a vertical direction, and a control unit arranged to control the movement mechanism unit such that the height of the first measurement axis at the time of first measurement by the first measurement unit becomes almost the same as the height of the second measurement axis at the time of second measurement by the second measurement unit.

BEST MODE FOR CARRYING OUT THE INVENTION

Figure 1A:
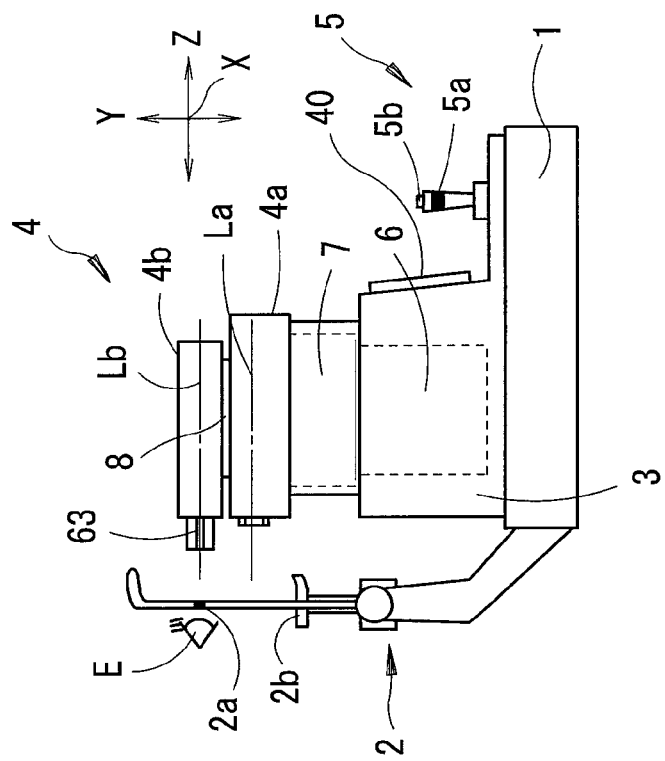
FIGS. 1A and 1B are schematic external views showing an ophthalmic apparatus according to a preferred embodiment of the present invention.
Figure 1B:
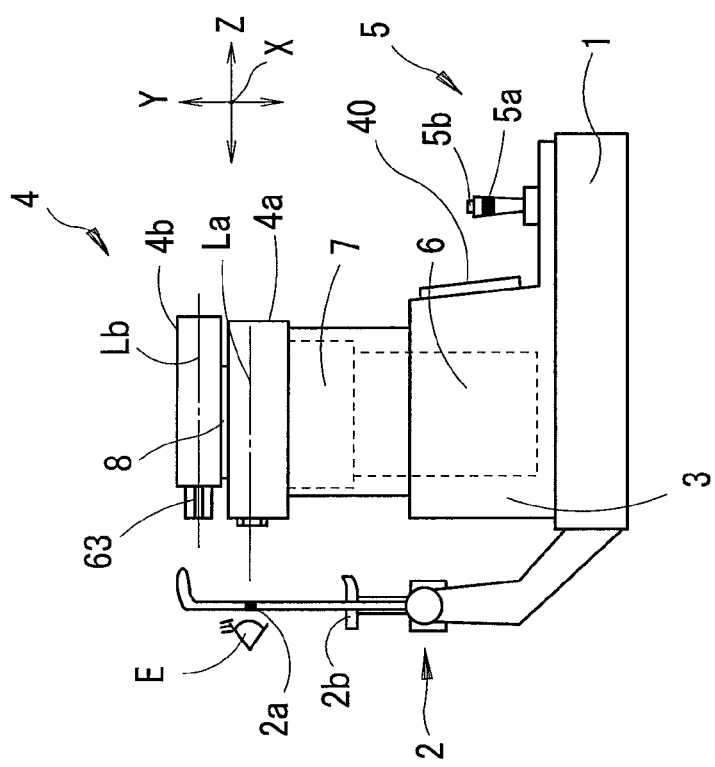

A detailed description of a preferred embodiment of the present invention is provided below with reference to the accompanying drawings. In this preferred embodiment of the present invention, a multifunction ophthalmic apparatus for performing measurement of eye refractive power, a corneal shape and intraocular pressure is explained as an example. FIGS. 1A and 1B are schematic external views showing an ophthalmic apparatus according to the preferred embodiment of the present invention. FIG. 1A shows a state of the apparatus at the time of measurement of eye refractive power and a corneal shape, and FIG. 1B shows a state of the apparatus at the time of measurement of intraocular pressure.

The ophthalmic apparatus comprises a base 1, a face (head) supporting unit 2 attached to the base 1, a mobile base 3 placed so as to be movable on the base 1, and a measurement unit 4 placed so as to be movable on the mobile base 3. The measurement unit 4 comprises a first measurement unit 4a for performing measurement of eye refractive power and a corneal shape of an examinee's eye E, and a second measurement unit 4b for performing noncontact measurement of intraocular pressure of the examinee's eye E, which is placed above the first measurement unit 4a. To be specific, in the measurement unit 4, the first measurement unit 4a and the second measurement unit 4b are placed such that the heights of a measurement optical axis (a measurement axis) La and a measurement optical axis (a measurement axis) Lb of the respective measurement units 4a and 4b are different from each other (the optical axis Lb is positioned higher than the optical axis La). The face supporting unit 2 comprises a chin rest 2b which is movable vertically and on which a chin of the examinee is placed.

The measurement unit 4 is arranged to be moved in an up/down direction (a vertical direction: a Y-direction in FIGS. 1A and 1B) with respect to the eye E of the examinee whose face is fixed to the face supporting unit 2 by the use of a Y-movement mechanism unit 6 which is provided to the mobile base 3. The measurement unit 4 is arranged such that the height of the optical axis La of the first measurement unit 4a is adjusted to almost the same height as the eye E by the Y-movement mechanism unit 6 in response to a changeover (a shift) to an eye refractive power and corneal shape measurement mode, and that the height of the optical axis Lb of the second measurement unit 4b is adjusted to almost the same height as the eye E by the Y-movement mechanism unit 6 in response to a changeover (a shift) to an intraocular pressure measurement mode. Hence, it is necessary to secure a movement amount (a driving amount) of the Y-movement mechanism unit 6 so as to be as wide as or wider than the distance between the optical axis La and the optical axis Lb, and further it is preferable to secure the movement amount so as to be in a range that automatic alignment of the first measurement unit 4a or the second measurement unit 4b with respect to the eye E is performed smoothly in each of the measurement modes.

In addition, the measurement unit 4 is arranged to be moved in a right/left direction (a horizontal direction: an X-direction in FIGS. 1A and 1B) and in a back/forth direction (a horizontal direction: a Z-direction in FIGS. 1A and 1B) with respect to the eye E of the examinee whose face is fixed to the face supporting unit 2 by the use of an XZ-movement mechanism unit 7 which is provided above the Y-movement mechanism unit 6. Accordingly, the measurement unit 4 is movable in the X-, Y- and Z-directions three-dimensionally. For example, the Y-movement mechanism unit 6 and the XZ-movement mechanism unit 7 comprise an X table which is movable in the X-direction, a Y table 604 (see FIG. 2) which is movable in the Y-direction and a Z table which is movable in the Z-direction, where the X table is placed on the Y table and the Z table is placed on the X table while the measurement unit 4 is mounted on the Z table, and the X, Y and Z tables are arranged to be moved by their respective motors and other members. For these three-dimensional movement mechanism units, known mechanism units can be used, so that detailed descriptions thereof are omitted.

The second measurement unit 4b is arranged to be moved in the Z-direction with respect to the first measurement unit 4a by the use of a Z-movement mechanism unit 8. To be specific, the second measurement unit 4b is arranged to be moved toward the eye E (moved forward) in response to a changeover (a shift) to the intraocular pressure measurement mode, and to be moved away from the eye E (moved backward) in response to a changeover (a shift) to the eye refractive power and corneal shape measurement mode.

The mobile base 3 is arranged to slide in the X-direction and the Z-direction on the base 1 through tilting operation of a joystick 5. The measurement unit 4 is arranged to be moved in the Y-direction by the use of the Y-movement mechanism unit 6 through rotating operation of a rotation knob 5a. A measurement starting switch 5b is provided at the top of the joystick 5. The mobile base 3 is provided with a monitor 40.

Figure 2:
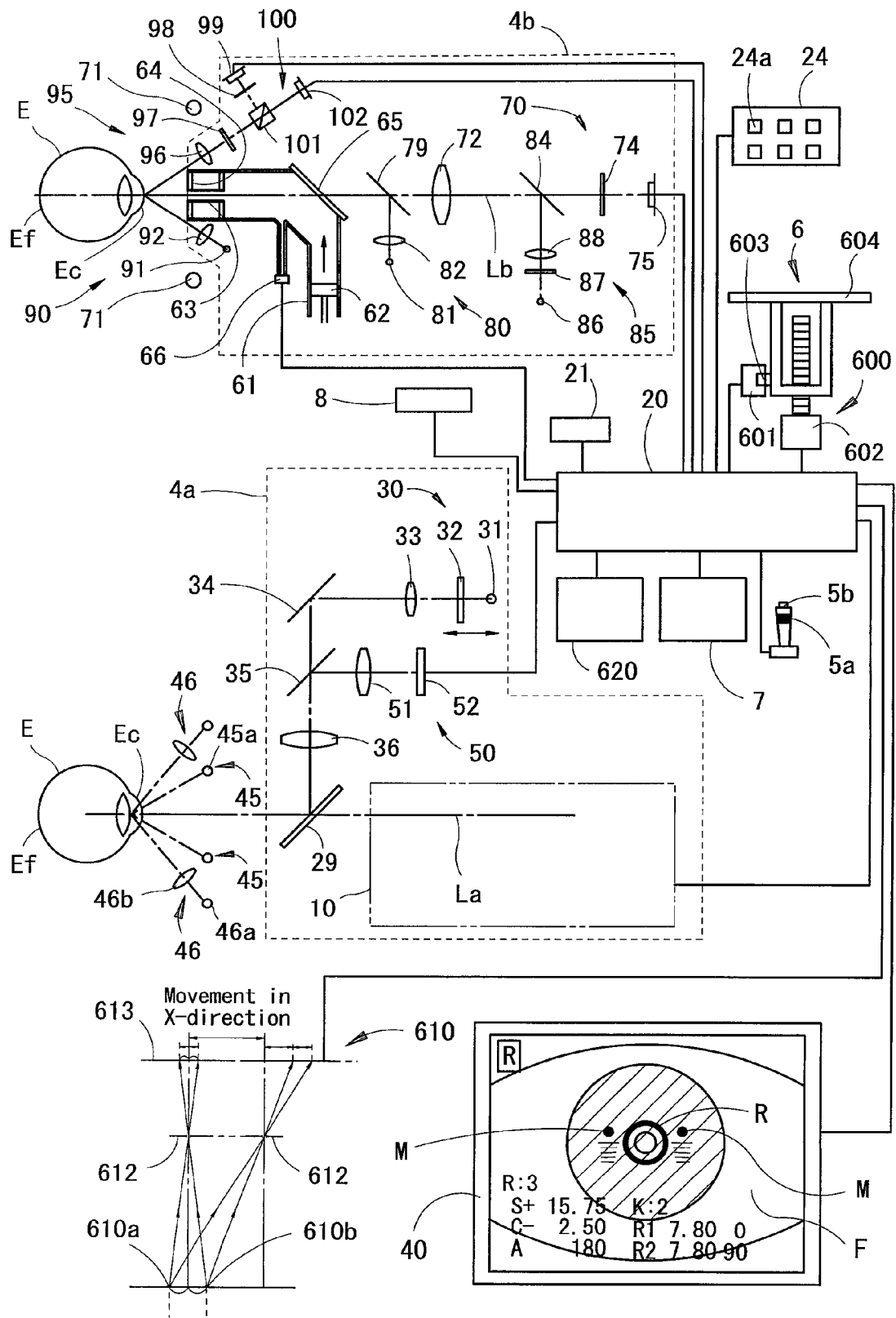
FIG. 2 is a view showing a schematic configuration of an optical system, a control system and other constituent elements of the ophthalmic apparatus.

FIG. 2 is a view showing a schematic configuration of an optical system, a control system and other constituent elements of the ophthalmic apparatus.

A description of an optical system of the first measurement unit 4a is provided first. An eye refractive power measurement optical system 10 for performing measurement of the eye refractive power of the eye E comprises a projection optical system having an infrared light source for projecting a spot-shaped measurement target (measurement light) onto a fundus Ef of the eye E, and an image-pickup optical system having a two-dimensional image-pickup element for picking up (detecting) a ring-shaped image of the measurement target (a fundus reflection image) (see U.S. Patent Publication No. 2005/0157261 corresponding to Japanese Patent Application Unexamined Publication No. 2005-185523). Output from the image-pickup element is inputted to a calculation and control unit 20. The eye refractive power measurement optical system 10 is not limited to an optical system having a configuration as described above, and a known optical system may be used.

A fixation target presenting optical system 30 comprises a visible light source 31, a fixation target plate 32, a projection lens 33, a total reflection mirror 34, a dichroic mirror 35 which has a property of transmitting visible light and reflecting infrared light, and an objective lens 36 for observation, which are placed on the optical axis La in a reflecting direction of a half mirror 29 which is placed on the optical axis La of the measurement optical system 10. The light source 31 is placed at a position optically conjugate with the fundus Ef. The light source 31 and the fixation target plate 32 are arranged to be movable in a direction of the optical axis La in order to fog the eye E.

A projection optical system 45 having an infrared light source 45a for projecting a ring-shaped measurement target (measurement light) onto a cornea Ec of the eye E in order to measure the corneal shape, and a projection optical system 46 having infrared light sources 46a and collimator lenses 46b for projecting alignment targets (alignment light) at an infinite distance onto the cornea Ec in order to detect an alignment state of the first measurement unit 4a in the Z-direction with respect to the eye E are placed in front of the half mirror 29 so as to be laterally symmetrical with respect to the optical axis La. The projection optical system 45 doubles as an optical system for projecting an alignment target (alignment light) at a finite distance which is used in order to detect an alignment state of the first measurement unit 4a in the X-, Y- and Z-directions with respect to the eye E, and as an optical system for illuminating an anterior segment of the eye E.

An observation optical system 50 shares the half mirror 29, the objective lens 36 and the dichroic mirror 35 with the fixation target presenting optical system 30, and comprises an image-pickup lens 51 and a two-dimensional image-pickup element 52 which are placed on the optical axis La in a reflecting direction of the dichroic mirror 35. Output from the image-pickup element 52 is inputted to the calculation and control unit 20. Thus, an image of the anterior segment of the eye E is picked up by the image-pickup element 52 and displayed on the monitor 40. The observation optical system 50 doubles as an optical system for picking up (detecting) an image of the ring-shaped measurement target (a corneal reflection image) doubling as an image of the alignment target at the finite distance (a corneal reflection image), and an image of the alignment targets at the infinite distance (a corneal reflection image).

Next, an air (fluid) blowing mechanism unit provided in the second measurement unit 4b will be described (see U.S. Pat. No. 6,537,215 corresponding to Japanese Patent Application Unexamined Publication No. 2002-34927). Air which is compressed inside a cylinder (an air compression chamber) 61 by a piston 62 moved by driving force of a rotary solenoid (not shown) is blown from a nozzle 63 to the cornea Ec. The nozzle 63 is held by transparent glass plates 64. A transparent glass plate 65 is provided behind the nozzle 63. Behind the glass plate 65, an optical system to be described later is placed. Pressure inside the cylinder 61 is detected by a pressure sensor 66. A signal from the pressure sensor 66 is inputted to the calculation and control unit 20.

A description of an optical system of the second measurement unit 4b is provided next (see U.S. Pat. No. 6,537,215 corresponding to Japanese Patent Application Unexamined Publication No. 2002-34927). When the second measurement unit 4b is used (at the time of the intraocular pressure measurement), the second measurement unit 4b is in a state where a tip of the nozzle 63 of the second measurement unit 4b is arranged to be thrust forward farther than a front surface of a housing of the first measurement unit 4a.

Four infrared light sources 71 for illuminating the anterior segment of the eye E are placed having the optical axis Lb coincident with an axis of the nozzle 63 (a centerline of the compressed air at the time of blowing) as their center. An observation optical system 70 comprises an objective lens 72 for observation, a filter 74 and a two-dimensional image-pickup element 75 which are placed on the optical axis Lb. The filter 74 has a property of transmitting light from the light sources 71 and light from a light source 81 to be described later, and not transmitting light from a light source 91 to be described later. Output from the image-pickup element 75 is inputted to the calculation and control unit 20. Thus, an image of the anterior segment of the eye E is picked up by the image-pickup element 75 and displayed on the monitor 40. The observation optical system 70 doubles as an optical system for picking up (detecting) an image of an alignment target (a corneal reflection image) which is used in order to detect an alignment state in the X- and Y-directions of the second measurement unit 4b with respect to the eye E.

A projection optical system 80 for projecting the alignment target (alignment light) onto the cornea Ec in order to detect the alignment state in the x- and Y-directions of the second measurement unit 4b with respect to the eye E comprises the infrared light source 81 and a projection lens 82 which are placed on the optical axis Lb in a reflecting direction of a half mirror 79 which is placed on the optical axis Lb. The light from the light source 81 is projected onto the cornea Ec from the front, and the alignment target image (the corneal reflection image) is picked up by the image-pickup element 75. A signal from the image-pickup element 75 is inputted to the calculation and control unit 20 and is used for the detection of the alignment state in the X- and Y-directions of the second measurement unit 4b. Besides, the corneal reflection image by the light source 71 may be used for the detection of the alignment state in the X- and Y-directions of the second measurement unit 4b (see U.S. Pat. No. 6,022,108 corresponding to Japanese Patent Application Unexamined Publication No. Hei 10-71122).

A fixation target presenting optical system 85 comprises a visible light source 86, a fixation target plate 87 and a projection lens 88 which are placed on the optical axis Lb in a reflecting direction of a dichroic mirror 84 having a property of transmitting infrared light and reflecting visible light which is placed on the optical axis Lb.

A projection optical system 90 for projecting a detection target (detection light) in order to detect a deformation state of the cornea Ec comprises the infrared light source 91 and a collimator lens 92. The projection optical system 90 doubles as an optical system for projecting an alignment target (alignment light) which is used in order to detect an alignment state in the Z-direction of the second measurement unit 4b with respect to the eye E.

A photo-receiving optical system 95 for detecting the deformation state of the cornea Ec comprises a photo-receiving lens 96, a filter 97, a pinhole plate 98 and a photodetector 99. The light from the light source 91 is made into substantially parallel light by the collimator lens 92 and is projected onto the cornea Ec in an oblique direction, and an image of the detection target (a corneal reflection image) by the light source 91 is photo-received by the photodetector 99. The filter 97 has a property of transmitting the light from the light source 91 and not transmitting the light from the light sources 71 and the light from the light source 81. The projection optical system 90 and the photo-receiving optical system 95 are placed such that a photo-receiving amount of the photodetector 99 becomes a maximum when the cornea Ec is in a predetermined deformation state (a flat state). A signal from the photodetector 99 is inputted to the calculation and control unit 20.

An optical system 100 for detecting an image of the alignment target which is used in order to detect the alignment state in the Z-direction of the second measurement unit 4b with respect to the eye E shares the photo-receiving lens 96 and the filter 97 with the photo-receiving optical system 95, and comprises a one-dimensional position detector 102 which is placed in a transmitting direction of a half mirror 101. An image of the alignment target (a corneal reflection image) by the light source 91 enters also the position detector 102. A signal from the position detector 102 is inputted to the calculation and control unit 20, and is used for the detection of the alignment state in the Z-direction of the second measurement unit 4b.

Incidentally, in FIG. 2, the projection optical system 90 and the photo-receiving optical system 95 are illustrated such that they are placed in the up/down direction (the Y-direction) for the sake of illustration; however, they are actually placed in the right/left direction (the X-direction).

Next, the control system of the ophthalmic apparatus according to the preferred embodiment of the present invention will be described. The calculation and control unit 20 which is arranged to perform control of the entire apparatus, calculation of measurement values and other control is connected with the light sources, the image-pickup elements and other constituent elements of the first measurement unit 4a, the light sources, the image-pickup elements, the photodetector, the position detector, the pressure sensor and other constituent elements of the second measurement unit 4b, the rotation knob 5a, the measurement starting switch 5b, the Y-movement mechanism unit 6, the XZ-movement mechanism unit 7, the Z-movement mechanism unit 8, the monitor 40, a memory 21 which is arranged to store results of the measurement and other information, a switch unit (an input unit) 24 provided with various switches such as a measurement mode selecting switch 24a, and other constituent elements.

In addition, the calculation and control unit 20 is connected with a detecting unit 600 which is arranged to detect a height (a position in the Y-direction) of the measurement unit 4 arranged to be moved in the Y-direction by the Y-movement mechanism unit 6. For example, the detecting unit 600 comprises a photosensor 601 and a shielding plate 603 which are arranged to detect whether or not the height of the measurement unit 4 reaches a predetermined reference height (e.g., a lower limit height of the measurement unit 4, a center height (the center position) in a moving range in the Y-direction of the measurement unit 4), a motor 602 (e.g., a pulse motor and a brushless motor) that is a driving source of the Y-movement mechanism unit 6 and the number of revolutions of which is detectable, and other constituent elements. The calculation and control unit 20 detects the height of the measurement unit 4 (e.g., a height of the Y table 604) based on the reference height and the number of the revolutions of the motor 602.

In addition, the calculation and control unit 20 is connected with a detecting unit 610 arranged to detect a position in the X-direction and a detecting unit 620 arranged to detect a position in the Z-direction of the measurement unit 4 which is moved in the X- and Z-directions by the XZ-movement mechanism unit 7. The detecting unit 610 comprises two light sources 610a and 610b which are placed on the base 1, a slit plate 612 and a one-dimensional position detector 613 which are placed in the measurement unit 4 (see U.S. Pat. No. 5,764,341 corresponding to Japanese Patent Application Unexamined Publication No. Hei 09-149885). The calculation and control unit 20 obtains, based on a result of the detection of the detecting unit 610, information that the eye E being subjected to the measurement by the measurement unit 4 is either the right eye or left eye, and obtains a distance between pupils of the examinee based on a travel distance in the X-direction of the measurement unit 4 at the time of the measurement of the right and left eyes.

The operation of the ophthalmic apparatus having the above-described configuration will be described. The ophthalmic apparatus has a first measurement mode of performing only eye refractive power and corneal shape measurement (the eye refractive power and corneal shape measurement mode), a second measurement mode of performing only intraocular pressure measurement (the intraocular pressure measurement mode), and a third measurement mode of performing both of the eye refractive power and corneal shape measurement and the intraocular pressure measurement (the eye refractive power and corneal shape measurement mode+ the intraocular pressure measurement mode). In the third measurement mode, the eye refractive power and corneal shape measurement is firstly performed, and the intraocular pressure measurement is performed thereafter. This is because if the intraocular pressure measurement is performed first, an influence of the blow of the compressed air or something exerted on the eye E could remain in the following measurement. Hereinafter, the third measurement mode will be described. A case will be described where the eye refractive power and corneal shape measurement is performed on the right eye and the left eye in this order, and then the intraocular pressure measurement is performed on the left eye and the right eye in this order.

Figure 3A:
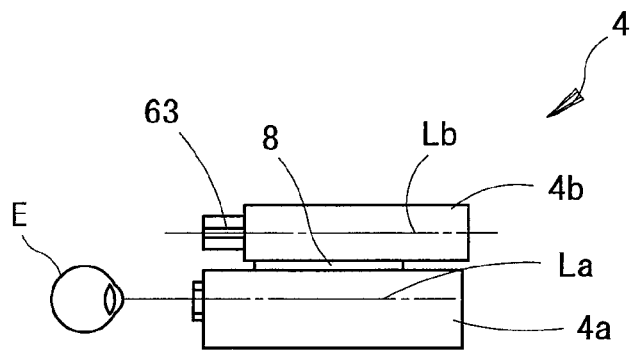
FIGS. 3A to 3C are views showing variations in the states of the ophthalmic apparatus at the time of measurement of eye refractive power and a corneal shape and at the time of measurement of intraocular pressure.

When the third measurement mode is selected with the use of the switch 24a, the apparatus firstly operates in the eye refractive power and corneal shape measurement mode. In this case, the calculation and control unit 20 initializes the height of the measurement unit 4 and adjusts it to a position of the height for eye refractive power and corneal shape measurement so that the eye refractive power and corneal shape measurement can be started smoothly. To be specific, the calculation and control unit 20 controls the measurement unit 4 to move in the Y-direction by driving the Y-movement mechanism unit 6, and adjust the height of the optical axis La of the first measurement unit 4a to almost the same height as the eye E (the height almost same as that of a height level mark 2a) of the examinee whose face is fixed to the face supporting unit 2. In addition, the calculation and control unit 20 controls the second measurement unit 4b to move backward farther than the first measurement unit 4a by driving the Z-movement mechanism unit 8 so that the tip of the nozzle 63 is prevented from making contact with the face of the examinee during the eye refractive power and corneal shape measurement. Accordingly, the measurement unit 4 is brought to a possible state of the eye refractive power and corneal shape measurement (see FIG. 3A). Further, the calculation and control unit 20 controls the measurement unit 4 to move in the X- and Z-directions by driving the XZ-movement mechanism unit 7, and initializes the positions in the X- and Z-directions of the measurement unit 4.

Next, alignment in the X-, Y- and Z-directions of the first measurement unit 4a with respect to the eye E (the right eye ER) is performed. The measurement unit 4 is moved to the side of the right eye ER by moving the mobile base 3 in the left direction with respect to the base 1 through the tilting operation of the joystick 5. Hence, an anterior-segment image F picked up by the image-pickup element 52 is displayed on the monitor 40 (see FIG. 2), so that rough alignment is performed through the operation of the joystick 5 and the knob 5b while the anterior-segment image F is observed. When a ring-shaped measurement target image (a corneal reflection image) R by the projection optical system 45, and alignment target images (corneal reflection images) M by the projection optical system 46 are brought into a state of being picked up by the image-pickup element 52, the calculation and control unit 20 controls the measurement unit 4 to move in the X-, Y- and Z-directions by driving the Y-movement mechanism unit 6 and the XZ-movement mechanism unit 7, and performs fine alignment of the first measurement unit 4a with respect to the right eye ER. In this case, the calculation and control unit 20 obtains a state of the alignment in the X- and Y-directions of the first measurement unit 4a with respect to the right eye ER based on the center position of the target image R. In addition, the calculation and control unit 20 obtains a state of the alignment in the Z-direction of the first measurement unit 4a with respect to the right eye ER based on a space between the target images M and a space of the target image R in a predetermined meridian direction (see U.S. Pat. No. 5,463,340 corresponding to Japanese Patent Application Unexamined Publication No. Hei 06-46999).

In the case of an automatic measurement mode, the measurement is automatically performed upon completion of the alignment. Meanwhile in the case of a manual measurement mode, the measurement is started by operating the switch 5b after the completion of the alignment.

The calculation and control unit 20 obtains eye refractive power of the right eye ER based on a ring-shaped measurement target image (a fundus reflection image) picked up by the image-pickup element of the measurement optical system 10 (see U.S. Patent Publication No. 2005/0157261 corresponding to Japanese Patent Application Unexamined Publication No. 2005-185523). Once a predetermined number of measurement values (e.g., three measurement values) of the eye refractive power except for a measurement error are obtained, the measurement is shifted to the corneal shape measurement.

Next, the calculation and control unit 20 obtains a corneal shape of the right eye ER based on the target image (the fundus reflection image) R picked up by the image-pickup element 52 (see U.S. Pat. No. 6,755,528 corresponding to Japanese Patent Application Unexamined Publication No. 2003-169778). Once a predetermined number of measurement values (e.g., three measurement values) of the corneal shape except for a measurement error are obtained, the measurement is shifted to eye refractive power and corneal shape measurement of the other eye E (the left eye EL).

Incidentally, the calculation and control unit 20 obtains a height (a position in the Y-direction) Er (yr) of the measurement unit 4 at the time of the eye refractive power and corneal shape measurement of the right eye ER based on results of detection by the detecting units 600, 610 and 620, and stores the height in the memory 21 while associating it with information that the eye E is the right eye ER. It is preferable to obtain the height Er when the alignment with the right eye ER is completed, or the measurement of the right eye ER is completed.

When the measurement of the right eye ER is completed, a message to that effect is displayed on the monitor 40. At this time, the calculation and control unit 20 controls the measurement unit 4 to reset its positions in the X- and Z-directions to predetermined initial positions thereof (e.g., the center positions in moving ranges in the X- and Z-directions of the measurement unit 4) by driving the XZ-movement mechanism unit 7.

The measurement unit 4 is moved to the side of the left eye EL by moving the mobile base 3 in the right direction with respect to the base 1 through the tilting operation of the joystick 5. Similarly to the case of the right eye ER, alignment in the X-, Y- and Z-directions of the first measurement unit 4a with respect to the left eye EL is performed, and eye refractive power and a corneal shape of the left eye EL are obtained.

Incidentally, the calculation and control unit 20 obtains a height (a position in the Y-direction) El (yl) of the measurement unit 4 at the time of the eye refractive power and corneal shape measurement of the left eye EL based on results of detection by the detecting units 600, 610 and 620, and stores the height in the memory 21 while associating it with information that the eye E is the left eye EL. It is preferable to obtain the height El when the alignment with the left eye EL is completed, or the measurement of the left eye EL is completed.

Once the eye refractive power and corneal shape measurement of the right eye ER and the left eye EL is completed, the operation mode is shifted to the intraocular pressure measurement mode. To be specific, once the predetermined number of the measurement values of the eye refractive power and the corneal shape of each of the right eye ER and the left eye EL are obtained, the calculation and control unit 20 automatically emits a signal for carrying out a changeover from the eye refractive power and corneal shape measurement mode to the intraocular pressure measurement mode.

Figure 3B:
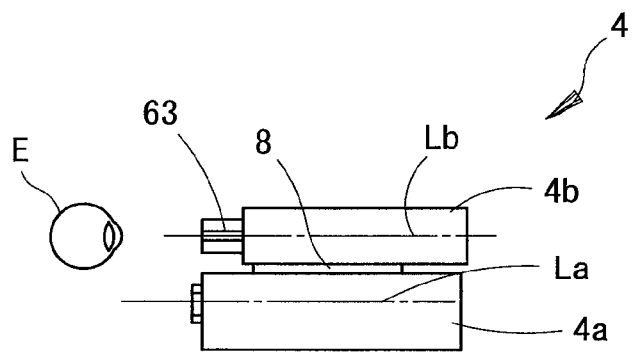

When the changeover signal to the intraocular pressure measurement mode is inputted, the calculation and control unit 20 initializes the height of the measurement unit 4 and adjusts it to a position of the height for the intraocular pressure measurement so that the intraocular pressure measurement can be started smoothly. To be specific, the calculation and control unit 20 controls the measurement unit 4 to move in the down direction by driving the Y-movement mechanism unit 6, and adjusts the height of the optical axis Lb of the second measurement unit 4b to almost the same height as the eye E of the examinee whose face is fixed to the face supporting unit 2 (see FIG. 3B). In other words, the calculation and control unit 20 controls the driving of the Y-movement mechanism unit 6 such that the height of the optical axis Lb in the intraocular pressure measurement mode becomes almost the same as the height of the optical axis La in the eye refractive power and corneal shape measurement mode.

When intraocular pressure measurement of the left eye EL is performed, the calculation and control unit 20 adjusts the height of the optical axis Lb to almost the same height as the left eye EL. To be specific, the calculation and control unit 20 reads out the height El (yl) stored in the memory 21 and a distance in the Y-direction between the optical axis La and the optical axis Lb which is prestored in the memory 21, and adjusts the height of the optical axis Lb in the intraocular pressure measurement of the left eye EL to almost the same height as the optical axis La in the eye refractive power and corneal shape measurement of the left eye EL.

In addition, when intraocular pressure measurement of the right eye ER is performed, the calculation and control unit 20 adjusts the height of the optical axis Lb to almost the same height as the right eye ER. To be specific, the calculation and control unit 20 reads out the height Er (yr) stored in the memory 21 and the distance in the Y-direction between the optical axis La and the optical axis Lb which is prestored in the memory 21, and adjusts the height of the optical axis Lb in the intraocular pressure measurement of the right eye ER to almost the same height as the optical axis La in the eye refractive power and corneal shape measurement of the right eye ER.

Figure 3C:
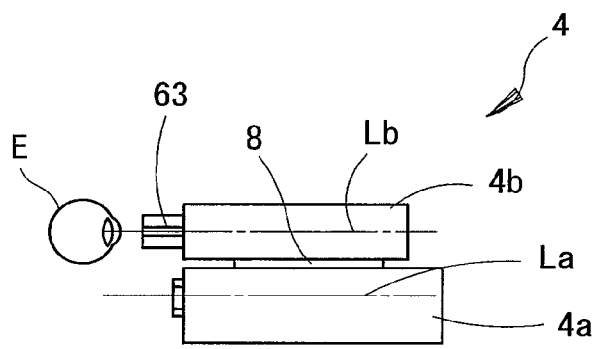

In addition, when the changeover signal to the intraocular pressure measurement mode is inputted, a message to move the mobile base 3 backward is displayed on the monitor 40. According to the displayed message, the mobile base 3 is moved backward with respect to the base 1 through the tilting operation of the joystick 5. When the calculation and control unit 20 detects that the measurement unit 4 is moved to a given back position based on the detection result by the detecting unit 620, the calculation and control unit 20 controls the second measurement unit 4b to move forward farther than the first measurement unit 4a by driving the Z-movement mechanism unit 8, and the tip of the nozzle 63 is thrust forward farther than the front surface of the housing of the first measurement unit 4a (See FIG. 3C).

Next, alignment in the X-, Y- and Z-directions of the second measurement unit 4b with respect to the left eye EL is performed. When an image of the alignment target (a corneal reflection image) by the light source 91 is brought into a state of entering the position detector 99, the calculation and control unit 20 controls the measurement unit 4 to move in the Z-direction by driving the XZ-movement mechanism unit 7, and performs fine alignment of the second measurement unit 4b with respect to the left eye EL. In addition, according to the changeover signal to the intraocular pressure measurement mode, the calculation and control unit 20 controls the monitor 40 to switch its display from the anterior-segment image by the image-pickup element 52 to an anterior-segment image by the image-pickup element 75. When an image of the alignment target (a corneal reflection image) by the light source 81 is brought into a state of being picked up by the image-pickup element 75, the calculation and control unit 20 controls the measurement unit 4 to move in the X- and Y-directions by driving the Y-movement mechanism unit 6 and the XZ-movement mechanism unit 7, and performs fine alignment of the second measurement unit 4b with respect to the left eye EL.

In the case of the automatic measurement mode, the measurement is automatically performed upon completion of the alignment. Meanwhile in the case of the manual measurement mode, the measurement is started by operating the switch 5b after the completion of the alignment.

The calculation and control unit 20 drives the rotary solenoid (not shown), whereby the piston 62 is moved and air compressed inside the cylinder 61 is blown from the nozzle 63 to the cornea Ec of the left eye EL. The cornea Ec is gradually deformed by the blow of the compressed air, and when the cornea Ec reaches the flat state, the light of the maximum photo-receiving amount enters the photodetector 99. The calculation and control unit 20 obtains intraocular pressure of the left eye EL based on the signal from the pressure sensor 66 and the signal from the photodetector 99 (see U.S. Pat. No. 6,537,215 corresponding to Japanese Patent Application Unexamined Publication No. 2002-34927). Once a predetermined number of measurement values (e.g., three measurement values) of the intraocular pressure except for a measurement error are obtained, the measurement is shifted to the intraocular pressure measurement of the other eye (the right eye ER).

When the measurement of the left eye EL is completed, a message to that effect is displayed on the monitor 40. At this time, the calculation and control unit 20 controls the measurement unit 4 to reset its positions in the x- and Z-directions to the predetermined initial positions by driving the XZ-movement mechanism unit 7.

The measurement unit 4 is moved to the side of the right eye ER by moving the mobile base 3 in the left direction with respect to the base 1 through the tilting operation of the joystick 5. Similarly to the case of the left eye EL, alignment in the X-, Y- and Z-directions of the second measurement unit 4b with respect to the right eye ER is performed, and intraocular pressure of the right eye ER is obtained.

By having the above-described configuration and the control, in each of the measurement performed by the use of the plurality of the measurement units which are placed so as to be stacked in the up/down direction (the Y-direction), the ophthalmic apparatus according to the preferred embodiment of the present invention is capable of performing the switching (height adjustment) of the measurement units quickly and automatically at the time of the shift of the measurement (the measurement mode). Accordingly, the alignment of each of the measurement units with respect to the examinee's eye can be performed, efficiently, and the eye refractive power and corneal shape measurement and the intraocular pressure measurement can be therefore performed efficiently. In particular, even in a case where the right eye and the left eye are different in height because of inclination of the examinee's face which is fixed to the face supporting unit 2 or another reason, the alignment and the measurement can be performed efficiently.

The order of the sequence of the measurement of the right eye and the measurement of the left eye is not limited to the above-described order. For example, it is also preferable that the eye refractive power and corneal shape measurement is performed on the right eye and the left eye in this order, and then the intraocular pressure measurement is performed on the right eye and the left eye in this order.

As a simple manner, it is also preferable that only when a changeover (shift) from the eye refractive power and corneal power measurement mode to the intraocular pressure measurement mode is carried out, the distance in the Y-direction between the optical axis La and the optical axis Lb which is prestored in the memory 21 is read out and the height of the optical axis Lb in the intraocular pressure measurement is adjusted to almost the same height as the optical axis La in the eye refractive power and corneal shape measurement. In this case, it is unnecessary to store the height Er (yr) and the height El (yl) of the measurement unit 4 at the time of the eye refractive power and corneal shape measurement in the memory 21 while associating them with the information that the eye E is either the right eye ER or the left eye EL.

In addition, although it is sufficient to store only the height Er (yr) and the height El (yl) in the Y-direction in the memory 21 if the automatic adjustment of the height of the first measurement unit 4a (the optical axis La) and the height of the second measurement unit 4b (the optical axis Lb) by the movement in the Y-direction of the measurement unit 4 is only performed as described above, automatic adjustment of the position in the X-direction of the first measurement unit 4a (the optical axis La) and the position in the X-direction of the second measurement unit 4b (the optical axis Lb) by the movement in the X-direction of the measurement unit 4 can be also performed by storing a position Er (xr) and a position El (xl) in the X-direction of the measurement unit 4 in the memory 21.

In this case, the detecting unit 610 arranged to detect the position in the X-direction of the measurement unit 4 comprises a photosensor, a shielding plate and a motor (e.g., a pulse motor and a brushless motor), similarly to the detecting unit 600. The calculation and control unit 20 detects the position in the X-direction of the measurement unit 4 based on a predetermined reference position in the X-direction (e.g., the center position in a moving range in the X-direction of the measurement unit 4) and the number of the revolutions of the motor.

The calculation and control unit 20 obtains the position Er (xr) in the X-direction of the measurement unit 4 at the time of the eye refractive power and corneal shape measurement of the right eye ER based on results of the detection by the detecting units 600 and 610, and stores the position Er (xr) in the memory 21 while associating it with information that the eye E is the right eye ER. When the measurement of the right eye ER is completed, the calculation and control unit 20 controls the measurement unit 4 to move in the right direction by driving the XZ-movement mechanism unit 7, whereby the measurement unit 4 is moved to the side of the left eye EL. In this case, the calculation and control unit 20 controls the measurement unit 4 to travel a distance in the right direction of, for example, two times as long as a distance from the reference position in the X-direction to the position Er (xr). Then, the calculation and control unit 20 obtains also the position El (xl) in the X-direction of the measurement unit 4 at the time of the eye refractive power and corneal shape measurement of the left eye EL based on results of the detection by the detecting units 600 and 610, and stores the position El (xl) in the memory 21 while associating it with information that the eye E is the left eye EL.

Once the eye refractive power and corneal shape measurement of the right eye ER and the left eye EL is completed and the changeover signal to the intraocular pressure measurement mode is inputted, the calculation and control unit 20 initializes the height of the measurement unit 4 and adjusts it to the position of the height for intraocular pressure measurement. To be specific, when performing the intraocular pressure measurement of the left eye EL, the calculation and control unit 20 reads out the height El (yl) stored in the memory 21 and the distance in the Y-direction between the optical axis La and the optical axis Lb which is prestored in the memory 21 and adjusts the height of the optical axis Lb in the intraocular pressure measurement of the left eye EL to almost the same height as the optical axis La in the eye refractive power and corneal shape measurement of the left eye EL. Meanwhile, when performing the intraocular pressure measurement of the right eye ER, the calculation and control unit 20 reads out the height Er (yr) stored in the memory 21 and the distance in the Y-direction between the optical axis La and the optical axis Lb which is prestored in the memory 21 and adjusts the height of the optical axis Lb in the intraocular pressure measurement of the right eye ER to almost the same height as the optical axis La in the eye refractive power and corneal shape measurement of the right eye ER.

In addition, the calculation and control unit 20 initializes the position in the X-direction of the measurement unit 4 and adjusts it to a position for intraocular pressure measurement. To be specific, when performing the intraocular pressure measurement of the left eye EL, the calculation and control unit 20 reads out the position El (xl) stored in the memory 21 and adjusts the position in the X-direction of the optical axis Lb in the intraocular pressure measurement of the left eye EL to almost the same position as the position in the X-direction of the optical axis La in the eye refractive power and corneal shape measurement of the left eye EL. Meanwhile, when performing the intraocular pressure measurement of the right eye ER, the calculation and control unit 20 reads out the position Er (xr) stored in the memory 21 and adjusts the position in the x-direction of the optical axis Lb in the intraocular pressure measurement of the right eye ER to almost the same position as the position in the X-direction of the optical axis La in the eye refractive power and corneal shape measurement of the right eye ER.

By having the above-described configuration and the control, the alignment of each of the measurement units with respect to the examinee's eye can be performed more efficiently, and the eye refractive power and corneal shape measurement and the intraocular pressure measurement can be therefore performed more efficiently.

It is also preferable that the automatic adjustment of the height of the first measurement unit 4a (the optical axis La) and the height of the second measurement unit 4b (the optical axis Lb) by the movement in the Y-direction of the measurement unit 4 is performed based on a difference between the position Er (yr) and the position El (yl) in the Y-direction and the distance in the Y-direction between the optical axis La and the optical axis Lb.

It is also preferable to perform the height adjustment of the measurement unit 4 when the calculation and control unit 20 detects that the measurement unit 4 is moved to the given back position after the completion of the eye refractive power and corneal shape measurement, not when the changeover signal to the intraocular pressure measurement mode is inputted.

Figure 4A:
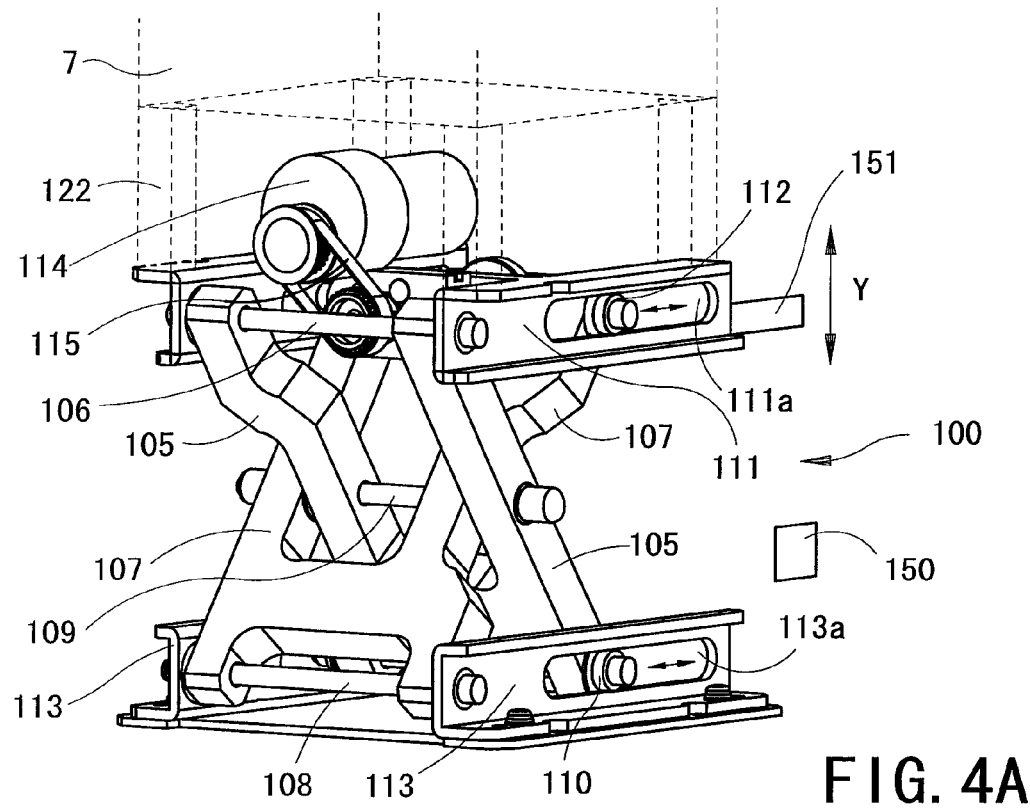
FIGS. 4A and 4B are views showing a schematic configuration of a parallel crank mechanism unit.
Figure 4B:
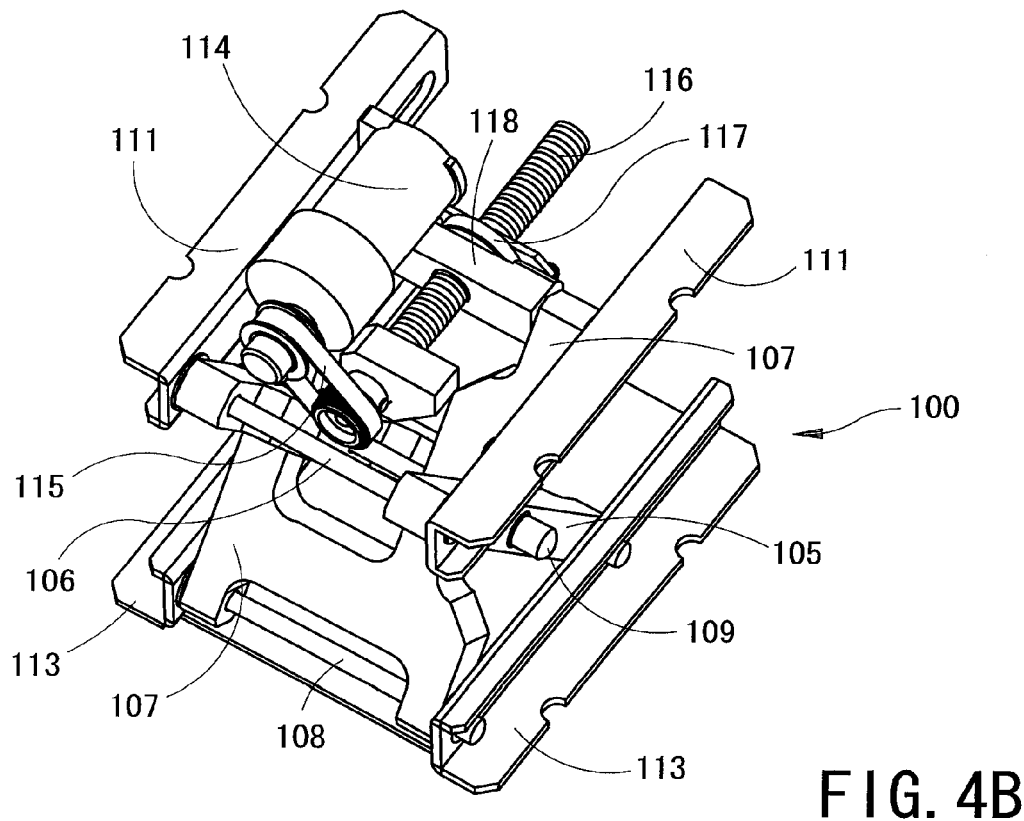

Next, a modified embodiment of the Y-movement mechanism unit 6 will be described. FIGS. 4A and 4B are views showing a schematic configuration of a parallel crank mechanism unit 100 which defines the Y-movement mechanism unit 6.

The parallel crank mechanism unit 100 capable of moving the measurement unit 4 in the Y-direction while keeping it in a horizontal position comprises a first link arm 105 and a second link arm 107 which are in the shape of the letter H and crossed saltirewise. Two upper portions of the first link arm 105 are supported rotatable about an upper shaft 106 which are fixed to two upper guide members 111 parallel to each other. Two lower portions of the second link arm 107 are supported rotatable about a lower shaft 108 parallel to the upper shaft 106, which is fixed to two lower guide members 113 parallel to each other and parallel respectively to the two upper guide members 111. The first link arm 105 and the second link arm 107 are supported rotatable about a middle shaft 109 which is parallel to the shafts 106 and 108.

Rollers 110 are attached turnable to two lower portions of the first link arm 105 such that they are movable in the horizontal direction along guide grooves 113a which are formed in the two lower guide members 113. Meanwhile, rollers 112 are attached turnable to two upper portions of the second link arm 107 such that they are movable in the horizontal direction along guide grooves 111a which are formed in the two upper guide members 111.

Above top surfaces of the upper guide members 111, the XZ-movement mechanism unit 7 is placed via coupling members 122. The measurement unit 4 is placed on the XZ-movement mechanism unit 7. A motor 114 (e.g., a pulse motor and a brushless motor) that is a driving source of the parallel crank mechanism unit 100 and the number of revolutions of which is detectable is placed in the space made by the coupling members 122. A rotation conveying member 118 is supported between the two upper portions of the second link arm 107, a nut 117 is fixed to the rotation conveying member 118, and a bolt 116 is inserted into the rotation conveying member 118 and the bolt 116. The revolution of the motor 114 is conveyed to the bolt 116 via a pulley attached to a rotation shaft of the motor 114, a pulley attached to the bolt 116, and a belt 115 which connects the pulleys, whereby the bolt 116 is rotated. By this rotation, the nut 117 and the rotation conveying member 119 move along the bolt 116, the second link arm 107 (the rollers 112) moves along the guide grooves 111a, and also the first link arm 105 (the rollers 110) moves along the guide grooves 113a.

In the parallel crank mechanism unit 100 having the above-described configuration, a bolt to be used for the movement in the Y-direction of the measurement unit 4 can be placed in the horizontal direction (the X- or Z-direction), so that the space in the Y-direction in the parallel crank mechanism unit 100 can be saved compared with a mechanism in which a bolt to be used for the movement in the Y-direction is placed in the vertical direction (the Y-direction). Besides, the parallel crank mechanism unit 100 is not limited to a parallel crank mechanism unit having the above-described configuration.

A photosensor 150 and a shielding plate 151 are used for detecting whether or not the height of the measurement unit 4 reaches a predetermined reference height (e.g., a lower limit height of the measurement unit 4, a center height (the center position) in the moving range in the Y-direction of the measurement unit 4).

Incidentally, in using the parallel crank mechanism unit 100 as the Y-movement mechanism unit 6, a movement amount in the Y-direction of the measurement unit 4 is smaller as the measurement unit 4 is higher in position while the movement amount in the Y-direction is larger as the measurement unit 4 is lower in position even if a revolution amount of the motor 114 does not vary. For this reason, when the measurement unit 4 is moved in the Y-direction through the rotating operation of the knob 5a, the movement amount in the Y-direction of the measurement unit 4 becomes smaller at the time of the eye refractive power and corneal shape measurement by the first measurement unit 4a while the movement amount in the Y-direction is larger at the time of the intraocular pressure measurement by the second measurement unit 4b even if the knob 5a is operated in the same manner.

Hence, the calculation and control unit 20 controls driving of the motor 114 such that movement velocity in the Y-direction of the measurement unit 4 is kept almost constant independently of the height of the measurement unit 4. For example, the height of the measurement unit 4 is detected and the driving of the motor 114 is controlled based on the detected height. In this case, it is essential only that a relation between the height of the measurement unit 4 such that the movement velocity in the Y-direction of the measurement unit 4 is kept almost constant independently of the height of the measurement unit 4 and a rotation drive signal of the motor 114 (e.g., the number of pulses of a pulse motor) should be obtained in advance by experiment, and the relation should be stored in the memory 21.

Figure 5:
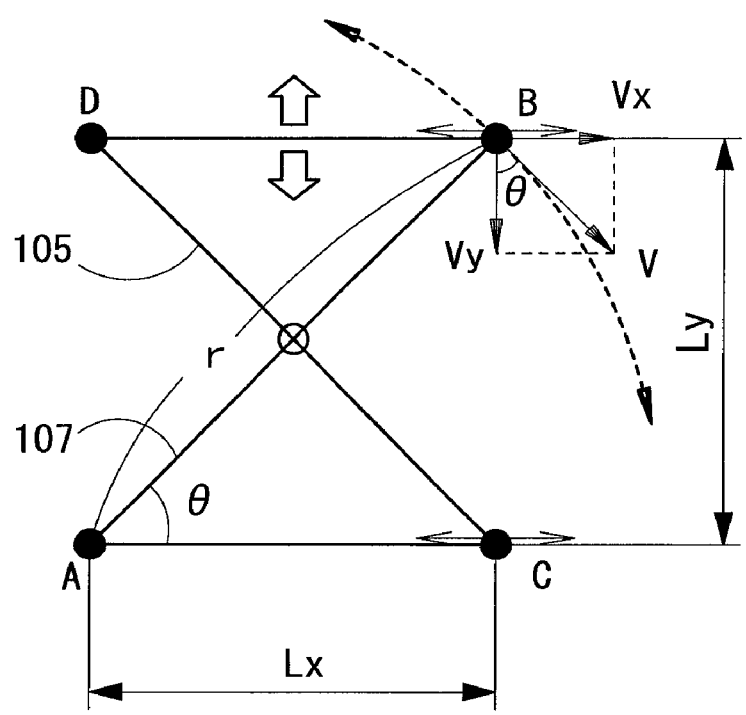
FIG. 5 is a diagram of the parallel crank mechanism unit.

It is also preferable that the height of the measurement unit 4 is detected not directly, i.e., detected indirectly. FIG. 5 is a diagram of the parallel crank mechanism unit 100. A length r indicates each of the length between the second link arm A-B and the length between the first link arm C-D, which is a known value. An angle $\theta$ indicates the angle which the second link arm A-B forms with a horizontal surface A-C of the parallel crank mechanism unit 100. A distance Ly indicates the distance in the vertical direction (the Y-direction) between the lower end A and the upper end B of the second link arm, and Ly=r sin $\theta$. A distance Lx indicates the distance in the horizontal direction (the X- or Z-direction) between the lower end A and the upper end B of the second link arm, and Lx=r cos $\theta$.

Assuming that movement velocity of the upper end B of the second link arm at the angle $\theta$ is V(t), movement velocity Vx in the horizontal direction=V(t)sin $\theta$, and the movement velocity Vy in the vertical direction=V(t)cos $\theta$. Hence, in order to make the movement velocity Vy constant, it is essential only that Equation 1: V(t)=k/cos $\theta$ should hold, where Vy is an arbitrary k. Accordingly, by varying the movement velocity V(t) according to the angle $\theta$ so as to satisfy Equation 1, the movement velocity in the Y-direction of the measurement unit 4 can be kept almost constant independently of the height of the measurement unit 4. Therefore, the calculation and control unit 20 controls the driving of the motor 114 based on Equation 1 stored in the memory 21 and the angle $\theta$ to be detected.

Owing to the configuration and the control described above, the movement amount in the Y-direction of the measurement unit 4 at the time of the eye refractive power and corneal shape measurement is made equal to the movement amount in the Y-direction of the measurement unit 4 at the time of the intraocular pressure measurement when the knob 5b is rotated in a similar manner both at the time of the eye refractive power and corneal shape measurement and at the time of the intraocular pressure measurement.

The revolution of the motor 114 may be varied in stages with each step of a given height of the measurement unit 4, not proportionally (linearly) to the height of the measurement unit 4.

It is also preferable that a range of the height of the measurement unit 4 is divided into a height range for the eye refractive power and corneal shape measurement mode and a height range for the intraocular pressure measurement mode, and the revolution of the motor 114 is varied according to a parameter which differs between the height ranges for the measurement modes. For example, the calculation and control unit 20 controls the revolution of the motor 114 to vary according to the selected measurement mode in order to make the movement velocity in the Y-direction of the measurement unit 4 at the time when the height of the optical axis La of the first measurement unit 4a in the eye refractive power and corneal shape measurement mode is in the vicinity of a given initial height (the height almost same as that of the height level mark 2a) equal to the movement velocity in the Y-direction of the measurement unit 4 at the time when the height of the optical axis Lb of the second measurement unit 4b in the intraocular pressure measurement mode is in the vicinity of a given initial height.

Figure 6A:
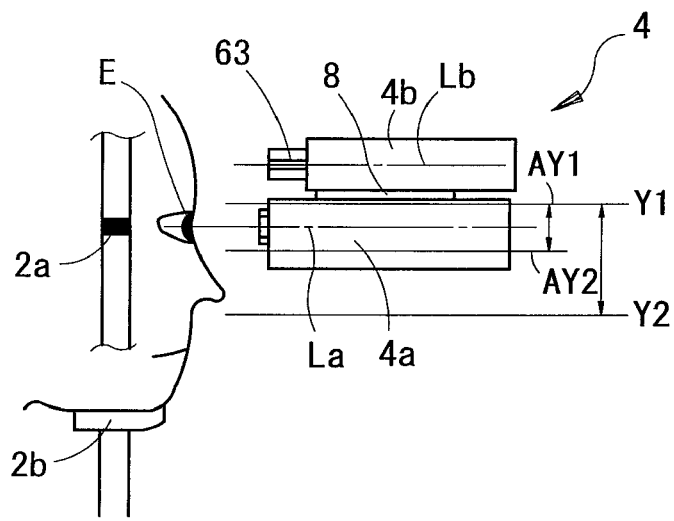
FIGS. 6A and 6B are views showing a movable range of a measurement unit in an up/down direction.
Figure 6B:
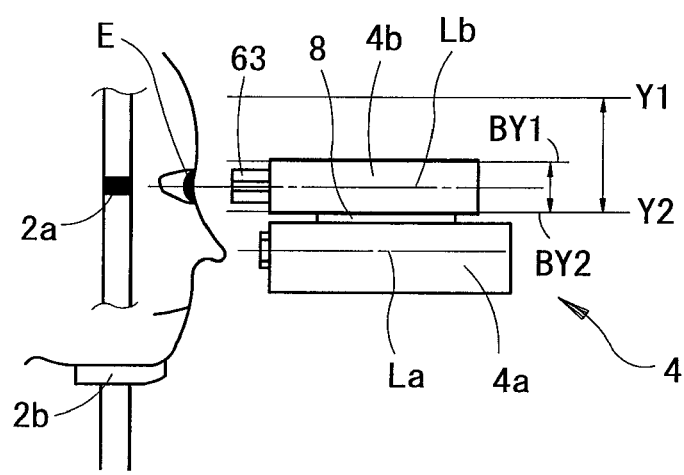

It is also preferable that movable ranges in the Y-direction of the measurement unit 4 are determined for the respective measurement modes. For example, as shown in FIGS. 6A and 6B, in a mechanically movable range in the Y-direction of the measurement unit 4 (a movable range of the measurement unit 4 by the Y-movement mechanism unit 6) (i.e., a range between an upper limit height Y1 and a lower limit height Y2), a movable range in the Y-direction of the optical axis La of the first measurement unit 4a in the eye refractive power and corneal shape measurement mode (a range between an upper limit height AY1 and a lower limit height AY2) and a movable range in the Y-direction of the optical axis Lb of the second measurement unit 4b in the intraocular pressure measurement mode (a range between an upper limit height BY1 and a lower limit height BY2) are established and prestored in the memory 21. The range between the upper limit height AY1 and the lower limit height AY2 and the range between the upper limit height BY1 and the lower limit height BY2 are each set to be narrower than the range between the upper limit height Y1 and the lower limit height Y2.

The movable range in the eye refractive power and corneal shape measurement mode is set to be a range which is predetermined with reference to the height of the optical axis La in a state almost the same as the given initial height (the height almost same as that of the height level mark 2a) (e.g., a range of ±16 mm in the Y-direction). This range is determined such that the measurement can be performed on various examinees without moving the chin rest 2b as long as the sizes of their faces are different only to some extent.

In addition, the movable range in the intraocular pressure measurement mode is set to be a range which is predetermined with reference to the height of the optical axis Lb in a state almost the same as the given initial height (the height almost same as that of the height level mark 2a) (e.g., a range of ±16 mm in the Y-direction).

In the eye refractive power and corneal shape measurement mode, when the calculation and control unit 20 detects that the measurement unit 4 reaches the upper limit height AY1 or the lower limit height AY2 based on the detection result by the detecting unit 610, it controls the Y-movement mechanism unit 6 to stop its driving so as not to move the measurement unit 4 any further in the up direction than the upper limit height AY1 or any further in the down direction than the lower limit height AY2. The calculation and control unit 20 controls also the monitor 40 to display a message that the measurement unit 4 reaches the upper limit height AY1 or the lower limit height AY2. In this case, it is essential only that a response such as readjusting the height of the chin rest 2b should be made.

Also in the intraocular pressure measurement mode, when the calculation and control unit 20 detects that the measurement unit 4 reaches the upper limit height BY1 or the lower limit height BY2 based on the detection result by the detecting unit 610, it controls the Y-movement mechanism unit 6 to stop its driving so as not to move the measurement unit 4 any further in the up direction than the upper limit height BY1 or any further in the down direction than the lower limit height BY2. The calculation and control unit 20 controls also the monitor 40 to display a message that the measurement unit 4 reaches the upper limit height BY1 or the lower limit height BY2. In this case too, it is essential only that a response such as readjusting the height of the chin rest 2b should be made.

Owing to the configuration and the control described above, the alignment of each of the measurement units with respect to the examinee's eye can be performed more efficiently, and the eye refractive power and corneal shape measurement and the intraocular pressure measurement can be therefore performed more efficiently.

Incidentally, it is also preferable that the lower limit height AY2 and the upper limit height BY1 are used as trigger points for the changeover between the measurement modes. To be specific, in the eye refractive power and corneal shape measurement mode, when the calculation and control unit 20 detects that the measurement unit 4 reaches the lower limit height AY2 based on the detection result by the detecting unit 610, the eye refractive power and corneal shape measurement mode is switched to the intraocular pressure measurement mode. Meanwhile, in the intraocular pressure measurement mode, when the calculation and control unit 20 detects that the measurement unit 4 reaches the upper limit height BY1 based on the detection result by the detecting unit 610, the intraocular pressure measurement mode is switched to the eye refractive power and corneal shape measurement mode. Thus, the changeover between the measurement modes can be performed easily.

Besides, it is also preferable that the detection that the measurement unit 4 reaches the upper limit height or the lower limit height is made based on a detection result by limit sensors which are provided respectively at the upper limit height and the lower limit height.

The invention claimed is:

1. An ophthalmic apparatus which performs measurement of a plurality of eye characteristics of an examinee's eye, the apparatus comprising:
    a first measurement unit comprising a first measurement system for performing measurement of a first characteristic of the examinee's eye;
    a first alignment detecting unit arranged to detect an alignment state of a first measurement axis of the first measurement system with respect to the examinee's eye;
    a second measurement unit comprising a second measurement system for performing measurement of a second characteristic of the examinee's eye;
    a second alignment detecting unit arranged to detect an alignment state of a second measurement axis of the second measurement system with respect to the examinee's eye;
    a measurement unit comprising the first and second measurement units and the first and second alignment detecting units, the first and second measurement units being placed such that a height of the first measurement axis of the first measurement system and a height the second measurement axis of the second measurement system are different from each other;

a movement mechanism unit arranged to move the measurement unit in a height direction, a right/left direction, and a back/forth direction; and measurement mode changeover means arranged to generate a changeover signal for carrying out a changeover between a first measurement mode for performing the measurement by the first measurement unit and a second measurement mode for performing the measurement by the second measurement unit;

a memory arranged to store information on a position of the measurement unit that is detected at the time of the measurement in the first measurement mode, the information comprising at least information on a position in the height direction of the measurement unit; and a control unit arranged to control the movement mechanism unit, based on the stored information on the position of the measurement unit in the memory, such that the height of the second measurement axis at the time of the measurement in the second measurement mode becomes the same as the height of the first measurement axis at the time of the measurement in the first measurement mode when a changeover from the first measurement mode to the second measurement mode is carried out based on the changeover signal.

2. The ophthalmic apparatus according to claim 1, wherein the movement mechanism unit comprises a parallel crank mechanism unit above which the measurement unit is placed, and the measurement unit is moved in the height direction by operating the parallel crank mechanism unit.

3. The ophthalmic apparatus according to claim 2, wherein the movement mechanism unit comprises a motor arranged to operate the parallel crank mechanism unit, and the control unit varies a revolution amount per unit time of the motor between the first measurement mode and the second measurement mode.

4. The ophthalmic apparatus according to claim 3, wherein the control unit controls the motor such that movement velocity in the height direction of the measurement unit is kept almost constant when the first measurement axis in the first measurement mode is at a reference height and the movement velocity of the measurement unit in the height direction and when the second measurement axis in the second measurement mode is at a reference height.

5. The ophthalmic apparatus according to claim 1, further comprising movable range setting means arranged to limit the movable range in the height direction of the measurement unit.

6. The ophthalmic apparatus according to claim 5, wherein the movable range in the first measurement mode and the movable range in the second measurement mode are different from each other.

7. The ophthalmic apparatus according to claim 1, wherein the stored information on the position of the measurement unit in the memory comprises information on a position of the measurement unit for each of right and left eyes.

8. The ophthalmic apparatus according to claim 1, wherein the stored information on the position of the measurement unit in the memory comprises information on a position in the right/left direction of the measurement unit for each of right and left eyes, and the control unit controls the movement mechanism unit based on the stored information on the position of the measurement unit in the memory.

9. The ophthalmic apparatus according to claim 1, wherein the stored information on the position of the measurement unit in the memory comprises information on a position in the right/left direction and the back/forth direction of the measurement unit for each of right and left eyes, and the control unit controls the movement mechanism unit based on the stored information on the position of the measurement unit in the memory.

* * * * *